US012623038B2

(12) United States Patent
Hattori

(10) Patent No.: US 12,623,038 B2
(45) Date of Patent: May 12, 2026

(54) CPAP DEVICE

(71) Applicant: Murata Manufacturing Co., Ltd., Kyoto (JP)

(72) Inventor: Atsushi Hattori, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 942 days.

(21) Appl. No.: 17/811,614

(22) Filed: Jul. 11, 2022

(65) Prior Publication Data
US 2022/0339395 A1     Oct. 27, 2022

Related U.S. Application Data

(63) Continuation of application No. PCT/JP2020/043921, filed on Nov. 26, 2020.

(30) Foreign Application Priority Data

Jan. 24, 2020     (JP) ................................. 2020-010019

(51) Int. Cl.
*A61M 16/00*          (2006.01)
*A61M 16/08*          (2006.01)
(Continued)

(52) U.S. Cl.
CPC .... *A61M 16/0066* (2013.01); *A61M 16/0816* (2013.01); *A61M 16/109* (2014.02); (Continued)

(58) Field of Classification Search
CPC .......... A61M 16/0066; A61M 16/0816; A61M 16/109; A61M 16/16; A61M 2205/0216; A61M 2205/123
See application file for complete search history.

(56) References Cited

U.S. PATENT DOCUMENTS

2007/0169776 A1     7/2007   Kepler et al.
2008/0072900 A1*    3/2008   Kenyon ............ A61M 16/0057
                                                                128/204.18
2017/0361053 A1*   12/2017   Dimatteo ............ A61M 16/024

FOREIGN PATENT DOCUMENTS

JP          2008-518640 A        6/2008
JP          2009-508647 A        3/2009

OTHER PUBLICATIONS

International Search Report for PCT/JP2020/043921 dated Jan. 19, 2021.

* cited by examiner

*Primary Examiner* — Joseph D. Boecker
(74) *Attorney, Agent, or Firm* — McDonald Hopkins LLC

(57)          ABSTRACT

An insertion-ejection opening opens in a housing case body of a housing case. A tank is inserted into and ejected from a housing space of the housing case body through the insertion-ejection opening of the housing case body. A portion of an upper-side internal surface of the housing case body forms a case slant surface slanted relative to a surface that is perpendicular to a height direction. In addition, the case slant surface faces toward a side of the insertion-ejection opening. A second discharge opening opens in the case slant surface. A portion of an external surface of the tank forms a tank slant surface slanted relative to the surface that is perpendicular to the height direction. A discharge tank aperture opens in the tank slant surface. In a state in which the tank is housed in the housing case body, the tank slant surface faces the case slant surface.

14 Claims, 6 Drawing Sheets

(51) Int. Cl.
*A61M 16/10*        (2006.01)
*A61M 16/16*        (2006.01)

(52) U.S. Cl.
CPC ..... *A61M 16/16* (2013.01); *A61M 2205/0216* (2013.01); *A61M 2205/123* (2013.01)

CPAP DEVICE

CROSS REFERENCE TO RELATED APPLICATION

This is a continuation of International Application No. PCT/JP2020/043921 filed on Nov. 26, 2020 which claims priority from Japanese Patent Application No. 2020-010019 filed on Jan. 24, 2020. The contents of these applications are incorporated herein by reference in their entireties.

BACKGROUND OF THE DISCLOSURE

Field of the Disclosure

The present disclosure relates to a continuous positive airway pressure (CPAP) device to deliver air sucked in the device into a respiratory tract of a user.

Description of the Related Art

In a CPAP device described in Patent Document 1, a blower to blow gas is built in a blowing unit. Additionally, the gas is made to flow into a housing case with activation of the blowing unit. A water storage tank is mounted inside the housing case. Additionally, in the housing case, a heater is mounted as a mechanism to promote the humidification in the tank.

On the housing case, an insertion-ejection opening for insertion and ejection of the tank opens. Additionally, on the housing case, a case aperture opens on a surface opposed to the insertion-ejection opening, besides the insertion-ejection opening. Further, a tank aperture providing communication between inside and outside of the tank opens on the tank. In a state in which the tank is mounted in the housing case, the case aperture and the tank aperture are placed so as to face each other, and circulation openings for the gas are made thereof.

Patent Document 1: Japanese Unexamined Patent Application Publication (Translation of PCT Application) No. 2009-508647

BRIEF SUMMARY OF THE DISCLOSURE

In the CPAP device described in Patent Document 1, as described above, the surface of the housing case opposed to the insertion-ejection opening is opened. Accordingly, when the tank is inserted into the housing case, the tank aperture of the tank is pressed against the case aperture of the housing case, so that both are prone to be sealed. In such a CPAP device as described in Patent Document 1, however, it may be desirable to open the case aperture of the housing case on a surface that is other than the surface opposed to the insertion-ejection opening. In this case, there is a concern that a force at a time of insertion of the tank into the housing case cannot be utilized as a force to cause close contact between the tank aperture of the tank and the case aperture of the housing case and that a gap may be consequently made between the tank aperture and the case aperture.

In order to solve the above-described problem, an aspect of the present disclosure is a CPAP device that includes a blowing unit including a built-in blower, a housing case including the blowing unit, a water storage tank to be housed in a housing space of the housing case, and a humidification promotion mechanism to vaporize water stored in the tank. The housing case includes an insertion-ejection opening for insertion and ejection of the tank. A portion of an internal surface of the housing case forms a first surface that is slanted relative to a surface perpendicular to an insertion-ejection direction for the tank through the insertion-ejection opening and that faces toward a side of the insertion-ejection opening. A portion of an external surface of the tank forms a first facing surface to come into direct or indirect contact with the first surface when the tank is housed in the housing space. The first surface or a surface that is among internal surfaces of the housing case and that is surrounded by the first surface includes a first case aperture to provide communication between inside and outside of the housing case. The tank includes a first tank aperture to provide communication between inside and outside of the tank, in a position that faces the first case aperture when the tank is housed in the housing space.

According to an above-described configuration, insertion of the tank into the housing space of the housing case through the insertion-ejection opening brings the first facing surface of the tank into contact with the first surface of the housing case. With further insertion with a push of the tank in that state, the first facing surface of the tank is pressed against the first surface of the housing case, so that sealability between the first tank aperture and the first case aperture can be ensured even if the first surface is not the surface that is perpendicular to the insertion-ejection direction for the tank.

With the insertion of the tank into the housing case, the sealability between the first tank aperture and the first case aperture can be ensured.

DETAILED DESCRIPTION OF THE DISCLOSURE

Hereinbelow, an embodiment of a CPAP device to deliver air introduced in the device into a respiratory tract of a user will be described with reference to the drawings.

Figure 1:
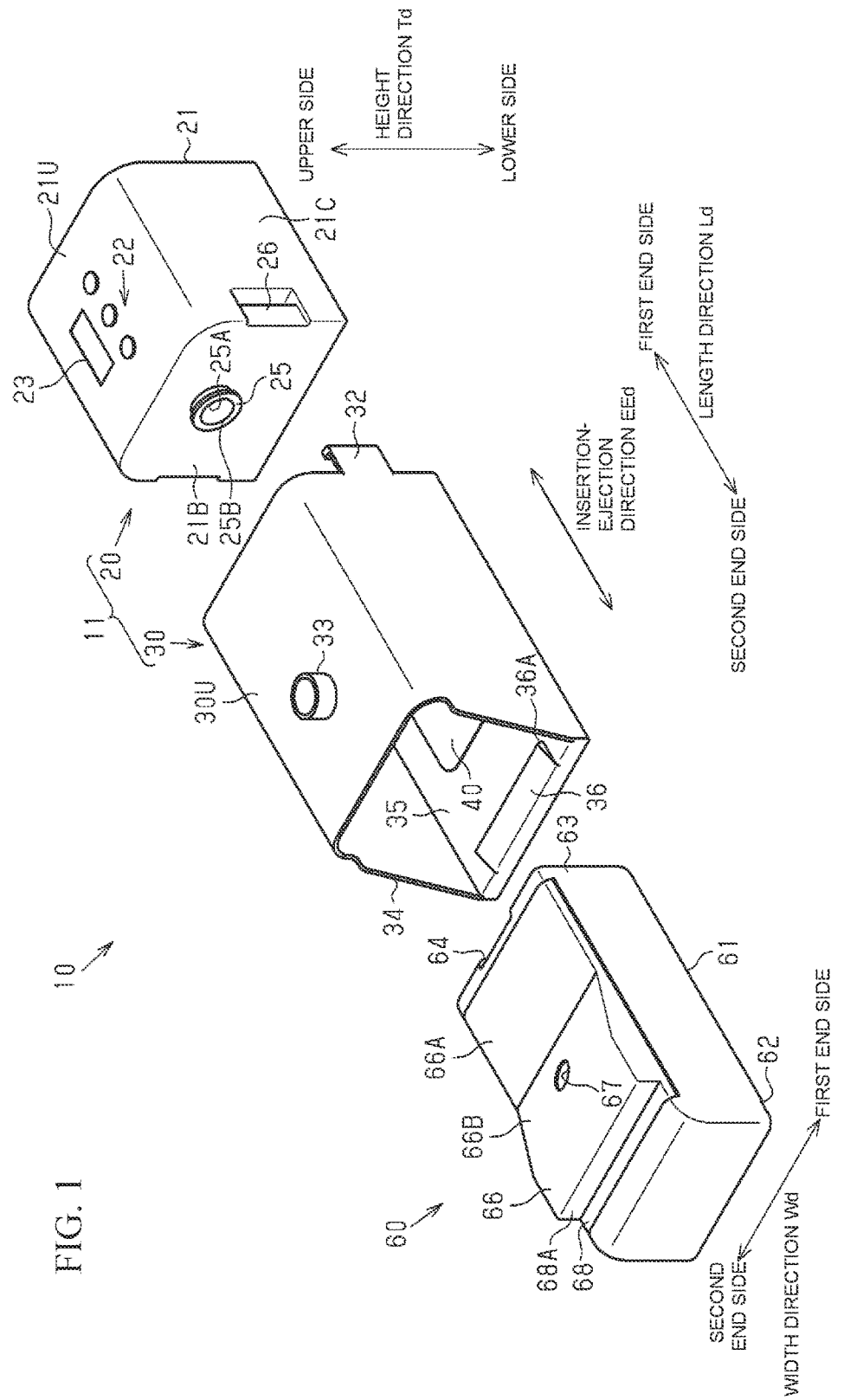
FIG. 1 is an exploded perspective view of a CPAP device.

As illustrated in FIG. 1, a blowing unit 20 of a CPAP device 10 includes a blower case 21 substantially shaped like a rectangular parallelepiped. A blower is built in the blower case 21, though illustration thereof is omitted.

An operation unit 22 to operate the blowing unit 20 is provided on an upper-side surface 21U of the blower case 21. In this embodiment, the operation unit 22 is made of three circular switches. All the switches are push button switches and operation of these enables to power-on and power-off of the blowing unit 20, change in settings, or the like. Incidentally, description below will be given as to a state in which the upper-side surface 21U of the blower case 21 is placed on an upper side with respect to a height direction Td.

In addition, a display unit 23 to display a state of the blowing unit 20 or the like is provided on the upper-side surface 21U of the blower case 21. In this embodiment, the display unit 23 is a rectangular liquid crystal display.

Figure 2:
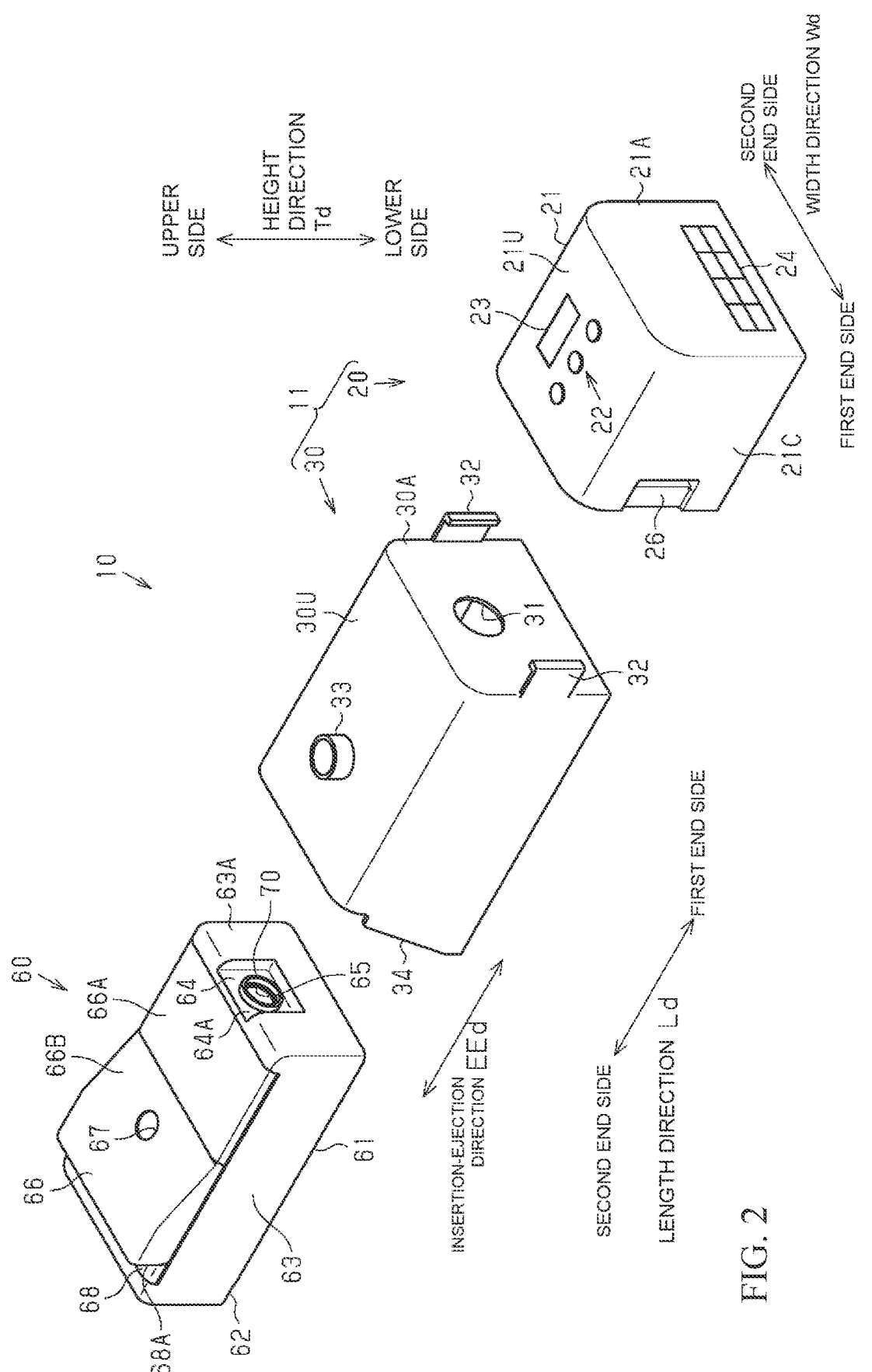
FIG. 2 is an exploded perspective view of the CPAP device as seen from an angle that is different from an angle of FIG. 1.

As illustrated in FIG. 2, a first introduction opening 24 to introduce air from outside of the blower case 21 into inside thereof opens in a first end surface 21A that is one of surfaces connected to the upper-side surface 21U of the blower case 21. A filter, not illustrated, to filter out dust or the like included in the air to be introduced into the blower case 21 is fixed to the first introduction opening 24. In description below, incidentally, a direction that is orthogonal to the height direction Td and orthogonal to the first end surface 21A is defined as a length direction Ld, and a side which the first end surface 21A faces is defined as a first end side while an opposite side thereto is defined as a second end side.

As illustrated in FIG. 1, a first discharge portion 25 to discharge air from the inside of the blower case 21 to the outside protrudes on a second end surface 21B that is among external surfaces of the blower case 21 and that is opposed to the first end surface 21A. The first discharge portion 25 is shaped like a cylinder and extends from the second end surface 21B toward the second end side in the length direction Ld. An opening of the first discharge portion 25 on a protruding tip-end side forms a first discharge opening 25A that is a discharge opening for gas from the blower case 21.

An end portion of the first discharge portion 25 on the second end side in the length direction Ld slightly extends toward an outer side portion in radial directions from the cylinder. In addition, an end surface 25B of the first discharge portion 25 on the second end side in the length direction Ld is a surface perpendicular to the length direction Ld. The first discharge portion 25 is substantially placed at a center of the second end surface 21B. Though illustration is omitted, a flow path through which air circulates is defined in the blower case 21, and an upstream end of the flow path is connected to the first introduction opening 24. Meanwhile, the blower is mounted in the middle of the flow path, and a downstream end of the flow path is connected to the first discharge portion 25. Thus, the first discharge opening 25A provides communication between an external space of the blower case 21 on the first end side in the length direction Ld and an external space thereof on the second end side in the length direction Ld through the flow path and the first introduction opening 24.

With a direction orthogonal to both the height direction Td and the length direction Ld defined as a width direction Wd, a recessed portion 26 is sunk onto a first side surface 21C that is among the external surfaces of the blower case 21 and that faces toward a first end side in the width direction Wd. The recessed portion 26 is placed at an end of the first side surface 21C on the second end side in the length direction Ld. In addition, the recessed portion 26 is placed at a center of the blower case 21 with respect to the height direction Td. Meanwhile, a recessed portion 26 is similarly sunk onto a second side surface facing a side opposed to a side which the first side surface 21C faces.

Figure 3:
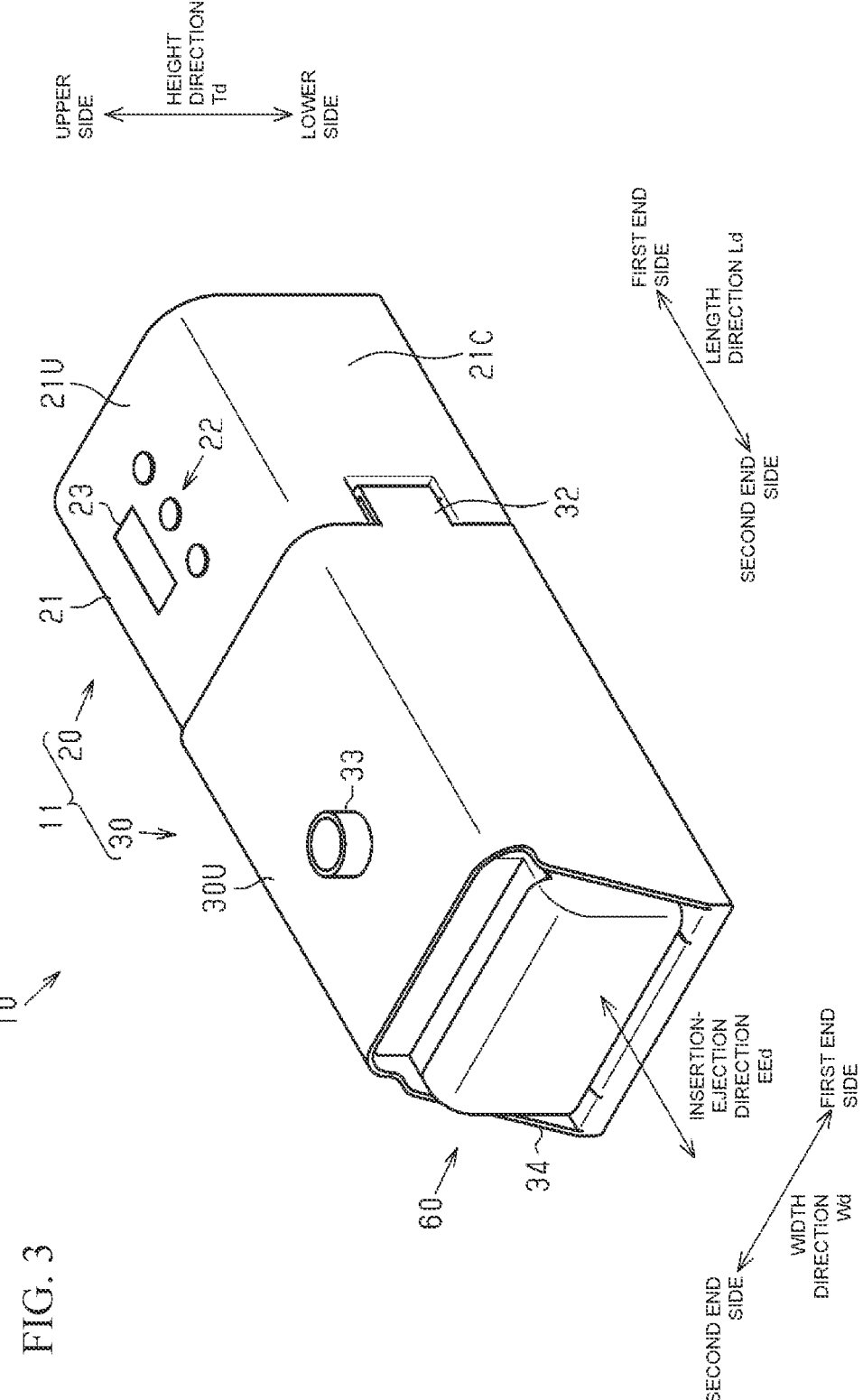
FIG. 3 is a perspective view of the CPAP device.

As illustrated in FIG. 3, a housing case body 30 is mounted onto the second end side of the blower case 21 in the length direction Ld. As illustrated in FIG. 1, the housing case body 30 is shaped like a rectangular parallelepiped elongated in the length direction Ld, as a whole. Sizes thereof along the height direction Td and the width direction Wd are substantially identical to sizes of the blower case 21 along the height direction Td and the width direction Wd. In this embodiment, a housing case 11 is made of the housing case body 30 and the blowing unit 20.

Figure 4:
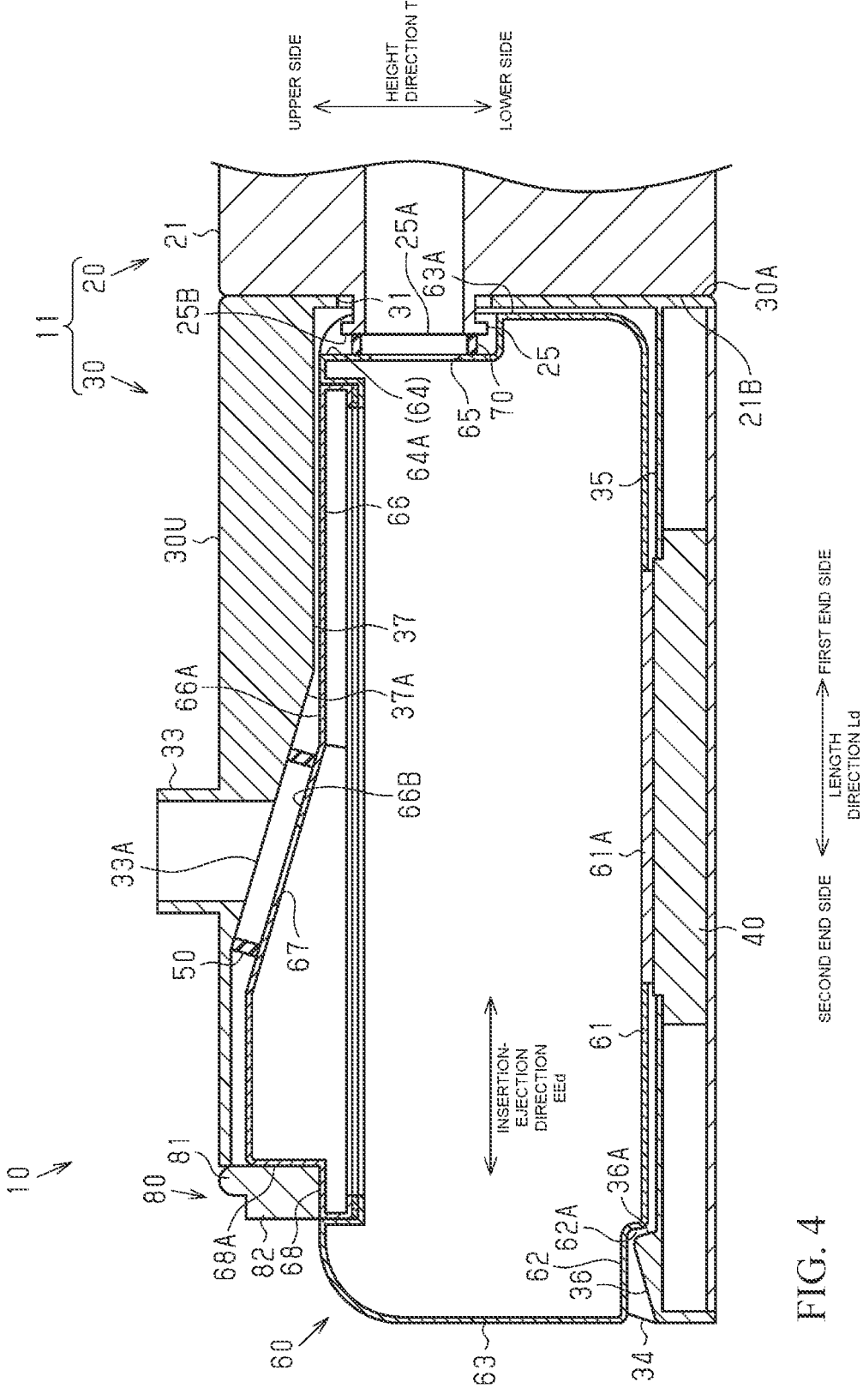
FIG. 4 is a sectional view of the CPAP device.

The housing case body 30 is shaped like a box having a housing space inside. As illustrated in FIG. 2, a second introduction opening 31 to introduce air from outside of the housing case body 30 into inside thereof opens in a first end surface 30A of the housing case body 30 on the first end side in the length direction Ld. The second introduction opening 31 is circular in plan view. As illustrated in FIG. 4, additionally, an outside diameter of the second introduction opening 31 is slightly greater than a maximum outside diameter of the first discharge portion 25 in the blower case 21. Additionally, the second introduction opening 31 is substantially placed at a center of the first end surface 30A and corresponds to a position of the first discharge portion 25 on the second end surface 21B of the blower case 21. When the housing case body 30 is mounted on the blower case 21, a tip-end portion of the first discharge portion 25 of the blower case 21 is inserted into the second introduction opening 31. Thus, an external surface of the first discharge portion 25 that is placed in the housing case body 30 functions as a portion of an internal surface of the housing case 11 as well. Additionally, in a state in which the housing case body 30 is mounted on the blower case 21, the first discharge opening 25A provides communication between the housing space inside the housing case 11 and an external space of the housing case 11 through the inside of the blower case 21.

As illustrated in FIG. 1, claw portions 32 substantially shaped like plates extend from both ends of the first end surface 30A of the housing case body 30 with respect to the width direction Wd toward the first end side in the length direction Ld. Tip-end portions of the claw portions 32 are bent toward a center side with respect to the width direction Wd. The claw portions 32 are placed on a center of the housing case body 30 with respect to the height direction Td. The claw portions 32 are adapted to be hooked on the recessed portions 26 of the blower case 21 in a state in which the first end surface 30A of the housing case body 30 and the second end surface 21B of the blower case 21 are placed so as to be in overall contact with each other, as illustrated in FIG. 3.

As illustrated in FIG. 1, a second discharge portion 33 to discharge air from the inside of the housing case body 30 to the outside thereof protrudes from an upper-side surface 30U of the housing case body 30. The second discharge portion 33 is shaped like a cylinder and extends to the upper side in the height direction Td from the upper-side surface 30U of the housing case body 30. As illustrated in FIG. 4, an opening of the second discharge portion 33 on an internal surface side of the housing case body 30 forms a second discharge opening 33A that is a discharge opening for gas from the inside of the housing case body 30. The second discharge opening 33A provides communication between the housing space inside the housing case body 30 and the external space. Incidentally, when the CPAP device 10 is used, one end of a hose is attached to the second discharge portion 33 and a mask is attached to the other end of the hose, though details are omitted.

As illustrated in FIG. 1, an insertion-ejection opening 34 opens in a portion of the housing case body 30 on the second end side in the length direction Ld. An opening edge of the insertion-ejection opening 34 is slanted relative to the surface that is perpendicular to the length direction Ld so as to lean toward the second end side in the length direction Ld at its lower side in the height direction Td.

A plate-like heater 40 is embedded in a bottom portion of the housing case body 30. An upper-side surface of the heater 40 with respect to the height direction Td is exposed from a lower-side internal surface 35 positioned on a lower side with respect to the height direction Td among internal surfaces of the housing case body 30. The heater 40 functions as a humidification promotion mechanism.

A convex portion 36 bulges to the upper side in the height direction Td on the lower-side internal surface 35 of the housing case body 30. The convex portion 36 is placed at an end of the lower-side internal surface 35 on the second end side in the length direction Ld. Additionally, the convex portion 36 extends across a range of approximately two thirds of the lower-side internal surface 35 along the width direction Wd at a center thereof with respect to the width direction Wd.

As illustrated in FIG. 4, a portion of an upper-side internal surface 37 of the housing case body 30 that is positioned on the upper side with respect to the height direction Td forms a case slant surface 37A slanted with respect to a surface that is perpendicular to the height direction Td. In this embodiment, a center portion of the upper-side internal surface 37 with respect to the length direction Ld forms the case slant surface 37A. In addition, the case slant surface 37A faces toward the insertion-ejection opening 34. The second discharge opening 33A described above opens in the case slant surface 37A. In the embodiment, the case slant surface 37A functions as a first surface, and the second discharge opening 33A functions as a first case aperture.

Figure 5:
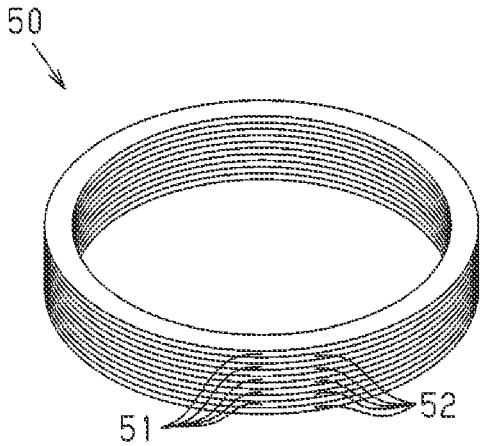
FIG. 5 is a perspective view of a first seal member.

A first seal member 50 shaped like a circular loop is mounted on the case slant surface 37A. The first seal member 50 surrounds the second discharge opening 33A from outside. As illustrated in FIG. 5, the first seal member 50 has a structure in which a plurality of layers are laminated with respect to a center axis direction of the first seal member 50. The plurality of layers are made by alternate stacking of hard rubber layers 51 and soft rubber layers 52 in the center axis direction. The hard rubber layers 51 and the soft rubber layers 52 are each shaped like a circular loop in plan view and have an identical outside diameter and an identical inside diameter. The hard rubber layers 51 have a comparatively large elastic modulus and are more resistant to expansion and contraction than the soft rubber layers 52. Meanwhile, the soft rubber layers 52 have an elastic modulus smaller than the hard rubber layers 51 have and are prone to be expanded and contracted compared with the hard rubber layers 51. Thus, the soft rubber layers 52 are made of a material having the elastic modulus different from the elastic modulus of the hard rubber layers 51, among the plurality of layers.

As illustrated in FIG. 3, a water storage tank 60 is housed in the housing space of the housing case body 30. The tank 60 is inserted into and ejected from the housing space of the housing case body 30 through the insertion-ejection opening 34 of the housing case body 30. In the embodiment, an insertion-ejection direction EEd for the tank 60 coincides with the length direction Ld. As illustrated in FIG. 2, the tank 60 is shaped like a box substantially having a shape of a rectangular parallelepiped, as a whole.

A bottom wall 61 of the tank 60 is shaped like a flat plate and is rectangular in plan view. As illustrated in FIG. 4, a center portion of the bottom wall 61 is a contact portion 61A that is to come into contact with the upper-side surface of the heater 40 in a state in which the tank 60 is housed in the housing space of the housing case body 30. Material of the contact portion 61A is metal. Meanwhile, material of portions of the bottom wall 61 except the contact portion 61A is resin.

A recessed portion 62 is sunk to the upper side in the height direction Td from a lower surface of the bottom wall 61 of the tank 60. The recessed portion 62 is placed at an end of an internal surface of the bottom wall 61 that is on the second end side in the length direction Ld. In addition, the recessed portion 62 extends entirely across the bottom wall 61 along the width direction Wd. When the tank 60 is housed in the housing space of the housing case body 30, the convex portion 36 of the housing case body 30 is fitted into the recessed portion 62. Then, a bump 36A of the convex portion 36 on the first end side in the length direction Ld comes into contact with a bump 62A of the recessed portion 62 that is a surface on the first end side in the length direction Ld from a side of the insertion-ejection opening 34 in the insertion-ejection direction EEd. In the embodiment, the convex portion 36 of the housing case body 30 functions as a stopper portion, and the recessed portion 62 of the tank 60 functions as a contact portion.

In the tank 60, as illustrated in FIG. 1, four side walls 63 extend to the upper side in the height direction Td from edges of the bottom wall 61. The side walls 63 extend from entirety of four sides of the bottom wall 61 and are shaped like a cartridge, as a whole. Material of the side walls 63 is resin. The four side walls 63 are substantially shaped like flat plates and have substantially identical sizes along the height direction Td.

As illustrated in FIG. 2, a sunken portion 64 that is quadrangular in plan view is sunk onto a first side wall 63A that is among the four side walls 63 and that is on the first end side in the length direction Ld. A perpendicular surface 64A positioned at the bottom of the sunken portion 64 extends in parallel with the first side wall 63A. That is, the perpendicular surface 64A is a surface that is perpendicular to the length direction Ld. The perpendicular surface 64A is a center portion of the first side wall 63A with respect to the width direction Wd and is placed in an upper-side portion thereof with respect to the height direction Td.

An introduction tank aperture 65 providing communication between inside and outside of the tank 60 opens in the perpendicular surface 64A. The introduction tank aperture 65 is circular in plan view and is substantially placed at a center of the perpendicular surface 64A.

A second seal member 70 shaped like a circular loop is mounted on the first end side of the perpendicular surface 64A in the length direction Ld. The second seal member 70 surrounds the introduction tank aperture 65. Material of the second seal member 70 is rubber that is elastically deformable.

Herein, with the tank 60 housed in the housing space of the housing case 11 as illustrated in FIG. 4, the perpendicular surface 64A of the tank 60 is parallel to the end surface 25B of the first discharge portion 25 that is the portion of the internal surface of the housing case 11 and faces the end surface 25B of the first discharge portion 25. Then, the perpendicular surface 64A of the tank 60 is in indirect contact with the end surface 25B that is the portion of the internal surface of the housing case 11, with the second seal member 70 interposed therebetween. In addition, the introduction tank aperture 65 faces the first discharge opening 25A. That is, the perpendicular surface 64A is brought into indirect contact with the end surface 25B with the second seal member 70 interposed therebetween and sealing is thereby attained between the first discharge opening 25A and the introduction tank aperture 65. In the embodiment, the end surface 25B functions as a second surface that is the portion of the internal surface of the housing case 11, and the perpendicular surface 64A of the tank 60 functions as a second facing surface. In addition, the introduction tank aperture 65 functions as a second tank aperture.

As illustrated in FIG. 1, a removable lid 66 is mounted on an upper side of the four side walls 63 with respect to the height direction Td in the tank 60. A portion of an external surface 66A of the lid 66 that is positioned on an outer side portion of the tank 60 forms a tank slant surface 66B slanted relative to the surface that is perpendicular to the height direction Td. In this embodiment, a center portion of the external surface 66A of the tank 60 with respect to the length direction Ld forms the tank slant surface 66B. An angle of the slant of the tank slant surface 66B to the surface that is perpendicular to the height direction Td is identical to an angle of the slant of the case slant surface 37A to the surface that is perpendicular to the height direction Td. Additionally, the tank slant surface 66B faces toward the first end side in the length direction Ld.

A discharge tank aperture 67 providing communication between the inside and the outside of the tank 60 opens in the tank slant surface 66B. The discharge tank aperture 67 is circular in plan view and is substantially placed at a center of the tank slant surface 66B.

Herein, with the tank 60 housed in the housing space of the housing case 11 as illustrated in FIG. 4, the tank slant surface 66B of the tank 60 is substantially parallel to the case slant surface 37A of the housing case body 30 and faces the case slant surface 37A. Then, the tank slant surface 66B is in indirect contact with the case slant surface 37A with the first seal member 50 interposed therebetween. In addition, the discharge tank aperture 67 faces the second discharge opening 33A. Accordingly, the discharge tank aperture 67 is placed at a position surrounded by the first seal member 50. That is, the tank slant surface 66B is in indirect contact with the case slant surface 37A with the first seal member 50 interposed therebetween, and a space between the second discharge opening 33A and the discharge tank aperture 67 is thereby sealed. In the embodiment, the tank slant surface 66B functions as a first facing surface, and the discharge tank aperture 67 functions as a first tank aperture.

Further, a recessed portion 68 is sunk to the lower side in the height direction Td on the lid 66. The recessed portion 68 is placed at an end of the lid 66 that is on the second end side in the length direction Ld. In addition, the recessed portion 68 is sunk entirely across the lid 66 along the width direction Wd.

As illustrated in FIG. 4, a turning stopper 80 is mounted on an upper end of the insertion-ejection opening 34 of the housing case body 30. The turning stopper 80 is capable of opening and closing a portion of the insertion-ejection opening 34 by rotation of a plate-like turning portion 82 about a rotation axis 81 extending in the width direction Wd, as a rotation axis. When the turning portion 82 is closed in the state in which the tank 60 is housed in the housing space of the housing case body 30, the turning portion 82 comes into contact with a bump 68A that is a surface of the recessed portion 68 of the tank 60 on the first end side in the length direction Ld, from the side of the insertion-ejection opening 34 in the insertion-ejection direction EEd. In the embodiment, the turning stopper 80 functions as a stopper portion, and the recessed portion 68 of the tank 60 functions as a contact portion. In FIGS. 1 to 3, incidentally, illustration of the turning stopper 80 is omitted.

Subsequently, functions and effects of the above embodiment will be described.

(1) According to the embodiment, insertion of the tank 60 into the housing space of the housing case 11 through the insertion-ejection opening 34 brings the tank slant surface 66B of the tank 60 into indirect contact with the case slant surface 37A of the housing case body 30 with the first seal member 50 interposed therebetween. With further insertion with a push of the tank 60 in that state, the tank slant surface 66B of the tank 60 is pressed against the case slant surface 37A of the housing case body 30, so that sealability between the discharge tank aperture 67 and the second discharge opening 33A can be ensured. Along with ensuring of the sealability, the mere insertion with a push of the tank 60 in the insertion-ejection direction EEd enables positioning of the tank 60, guided by the case slant surface 37A, with respect to the height direction Td as well.

(2) According to the embodiment, the heater 40 is placed to the lower side of the case slant surface 37A with respect to the height direction Td in the housing case body 30. Therefore, when the contact of the tank 60 with the case slant surface 37A causes the tank 60 to move to the lower side with respect to the height direction Td, close contact between the tank 60 and the heater 40 is attained. As a result, heating by the heater 40 of water stored in the tank 60 is facilitated.

(3) According to the embodiment, the first seal member 50 that is an elastic body is interposed between the case slant surface 37A and the tank slant surface 66B. Therefore, when the tank 60 is housed in the housing space of the housing case 11 by being pushed in the insertion-ejection direction EEd, the first seal member 50 is compressed. Accordingly, after the tank 60 is housed in the housing space of the housing case 11, a force by which the deformed first seal member 50 is going to be restored is exerted on the tank 60. As a result, the tank 60 is pressed toward the lower side with respect to the height direction Td. Thus, the contact portion 61A of the tank 60 can be brought into closer contact with the upper-side surface of the heater 40.

(4) According to the embodiment, the first seal member 50 has the laminated structure made of the plurality of layers made of rubber. When the tank 60 is pushed in the insertion-ejection direction EEd, therefore, the first seal member 50 undergoes shear deformation. Then, the presence of the layers having the small elastic modulus facilitates the deformation in a shearing direction, and the presence of the layers having the large elastic modulus provides resistance to compression in the center axis direction of the loop. Thus, the shear deformation can be facilitated, as a whole, while the sealability between the discharge tank aperture 67 and the second discharge opening 33A is ensured.

(5) According to the embodiment, the introduction tank aperture 65 of the tank 60 corresponding to the second tank aperture opens in the perpendicular surface 64A that is perpendicular to the insertion-ejection direction EEd, and the perpendicular surface 64A is in contact with the end surface 25B of the first discharge portion 25 that is the portion of the internal surface of the housing case 11, with the second seal member 70 interposed therebetween. Thus, a push of the tank 60 in the insertion-ejection direction EEd enables ensuring of sealability between the introduction tank aperture 65 and the first discharge opening 25A opening in the end surface 25B of the first discharge portion 25.

Further, the case slant surface 37A that functions as the first surface and the end surface 25B of the first discharge portion 25 that functions as the second surface face in different directions. Thus, the first discharge portion 25 and the second discharge portion 33 can be placed on the different surfaces. As a result, compared with the placement of the two discharge portions in an identical surface, a distance between the discharge portions can be increased, so that the prevention of the interference between the blower case 21 and the hose attached to the second discharge portion 33 is facilitated.

(6) According to the embodiment, after the first seal member 50 and the second seal member 70 are compressed by a push of the tank 60 in the insertion-ejection direction EEd, the seal members act to push back the tank 60 in order to recover from the deformation. Meanwhile, the housing case body 30 is provided with the turning stopper 80 and the bump 36A of the convex portion 36. These function as the stopper portions to be brought into contact with the tank 60 from the side of the insertion-ejection opening 34 in the insertion-ejection direction EEd. Therefore, even if the tank 60 is moved so as to come out through the insertion-ejection opening 34 in the insertion-ejection direction EEd, the bump 68A and the bump 62A functioning as the contact portions of the tank 60 come into contact with the stopper portions, so that the tank 60 can be prevented from coming out of the housing space of the housing case 11.

Each of the embodiments may be implemented with modifications as follows. The embodiment and the following modifications may be implemented in combination within a technically consistent range.

In the embodiment, a position where the blowing unit 20 is mounted is not limited to an upstream side of the housing case body 30. For instance, mounting on the second discharge portion 33 of the housing case body 30 is allowed. In this case, when the blower of the blowing unit 20 is activated, air is sucked in from inside of the housing case body 30 and the tank 60, so that gas is delivered into a user.

In the embodiment, the housing case 11 may be made only of the housing case body 30. In this case, it is sufficient if the second seal member 70 mounted on the perpendicular surface 64A of the tank 60 is brought into contact with the internal surface of the housing case body 30 where the second introduction opening 31 is opened. In this case, the second introduction opening 31 functions as a second case aperture to provide the communication between the inside and the outside of the housing case body 30.

In the embodiment, the insertion-ejection direction EEd is not limited to an example of the embodiment. For instance, the insertion-ejection direction EEd may coincide with the height direction Td or may be slanted relative to both the length direction Ld and the height direction Td. In this case, it is sufficient if the case slant surface 37A is slanted at least relative to the surface that is perpendicular to the insertion-ejection direction EEd.

In the embodiment, a manner in which the heater 40 is mounted in the housing case body 30 is not limited to the example of the embodiment. For instance, the heater 40 may be embedded in the housing case body 30 and may be exposed on the internal surface side of the housing case body 30.

In the embodiment, a mounting position of the heater 40 is not limited to the example of the embodiment. For instance, the heater 40 may be mounted on a side wall 63 of the housing case body 30 or may be mounted on the lid 66 of the housing case body 30. Incidentally, it is preferable that the heater 40 is positioned on a side opposed to the case slant surface 37A with the housing space of the housing case body 30 in between because the tank 60 is moved toward the heater 40 when the tank 60 is housed in the housing space of the housing case 11.

In the embodiment, the humidification promotion mechanism is not limited to the heater 40 to heat the tank 60. For instance, an ultrasonic generation device may be provided as the humidification promotion mechanism. In this case, the ultrasonic generation device is not necessarily required to be in contact with the tank 60, and efficient atomization of water in the tank 60 by ultrasonic waves and promotion of vaporization can be attained, providing that the ultrasonic generation device is provided so that a distance from the ultrasonic generation device to the water in the tank 60 may be of a desired value.

Figure 6:
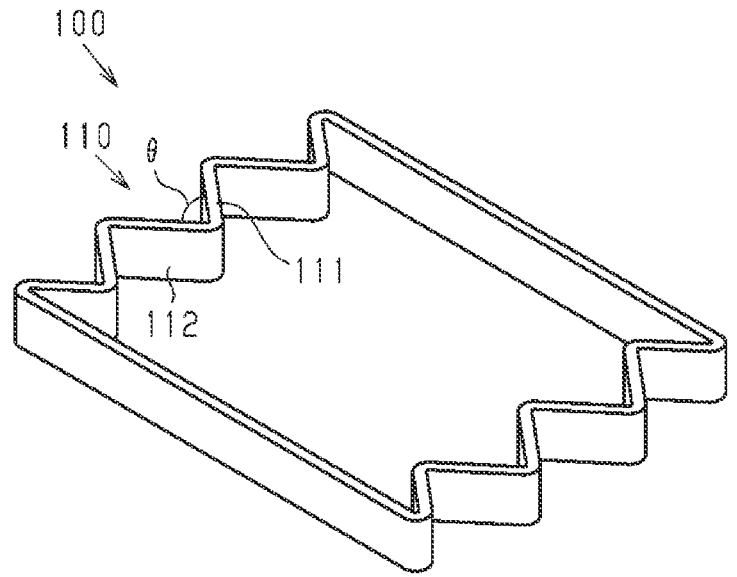
FIG. 6 is a perspective view of a first seal member in a modification.

In the embodiment, the structure of the first seal member 50 is not limited to the example of the embodiment. In an example illustrated in FIG. 6, for instance, a first seal member 100 is shaped like a quadrangular loop in plan view, as a whole, and has one pair of facing sides including bellows portions 110 shaped like bellows. The bellows portions 110 are made by alternate connection of first walls 111 and second walls 112 that extend in different directions, as seen in an axis direction of the loop. An angle θ made by the first wall 111 and the second wall 112 that adjoin is an acute angle. Employment of the first seal member 100 as such facilitates shear deformation and reduction in deformation in the center axis direction of the loop. Additionally, it is preferable for facilitation of the shear deformation that the first seal member 100 is mounted on the case slant surface 37A of the housing case body 30 so that an extending direction of the entire bellows portions 110 may coincide with the insertion-ejection direction EEd as seen in the height direction Td.

Figure 7:
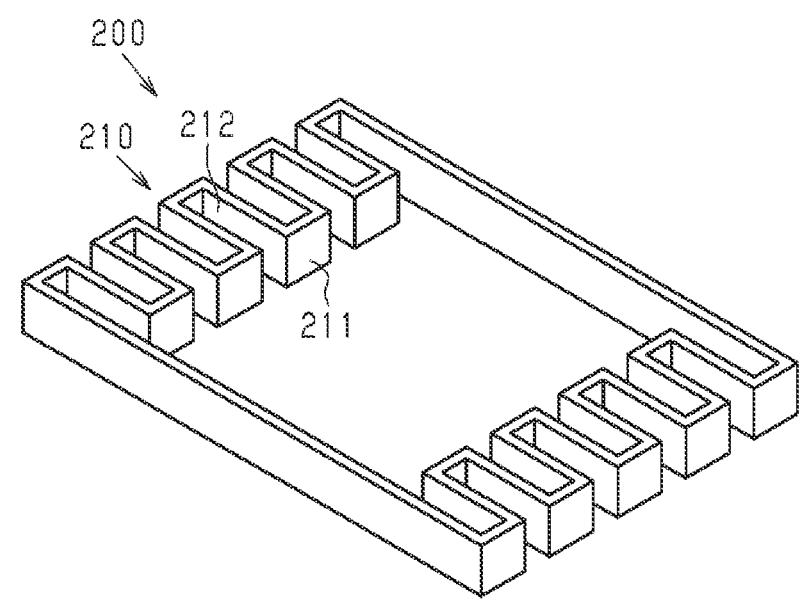
FIG. 7 is a perspective view of a first seal member in a modification.

In an example illustrated in FIG. 7, for instance, a first seal member 200 is shaped like a quadrangular loop in plan view, as a whole, and has one pair of facing sides including bellows portions 210 shaped like bellows. The bellows portions 210 are made by alternate connection of first walls 211 extending in a direction orthogonal to the other pair of facing sides and second walls 212 extending in a direction orthogonal to the first walls 211, as seen in an axis direction of the loop. A size of the first walls 211 along the extending direction is smaller than a size of the first seal member 200 along a thickness direction. Employment of the first seal member 200 as such facilitates shear deformation and reduction in deformation in the center axis direction of the loop. Additionally, it is preferable for the facilitation of the shear deformation that the first seal member 200 is mounted on the case slant surface 37A of the housing case body 30 so that an extending direction of the entire bellows portions 210 may coincide with the insertion-ejection direction EEd as seen in the height direction Td.

In the embodiment, a shape of the first seal member 50 is not limited to a shape like the loop. For instance, the first seal member 50 may be shaped like a letter of C. A portion of the tank slant surface 66B and a portion of the case slant surface 37A may be in direct contact with each other, and another portion of the tank slant surface 66B and another portion of the case slant surface 37A that are not in the direct contact may be in indirect contact with each other with the first seal member 50 interposed therebetween.

In the embodiment, a size of the first seal member 50 along the center axis direction of the loop is not limited to a uniform size. For instance, in case where the angle of the slant of the tank slant surface 66B to the surface that is perpendicular to the height direction Td is not parallel to the angle of the slant of the case slant surface 37A to the surface that is perpendicular to the height direction Td, it is sufficient if the size of the first seal member 50 along the center axis direction of the loop is appropriately adjusted. In this case, it is sufficient if a space between the discharge tank aperture 67 and the second discharge opening 33A is sealed by the first seal member 50.

In the embodiment, the first seal member 50 may be omitted. In this case, when the tank 60 is housed in the housing space of the housing case 11, a position of the tank 60 can be adjusted in a direction that is different from the insertion-ejection direction EEd, by direct contact of the tank slant surface 66B of the tank 60 with the case slant surface 37A of the housing case body 30.

In the embodiment, an orientation of the case slant surface 37A is not limited to the example of the embodiment. With a slant relative to the surface that is perpendicular to the insertion-ejection direction EEd and the orientation toward the side of the insertion-ejection opening 34 with respect to the insertion-ejection direction EEd, the sealability between the discharge tank aperture 67 and the second discharge opening 33A can be ensured when the tank 60 is inserted in the housing space of the housing case 11 in the insertion-ejection direction EEd.

Figure 8:
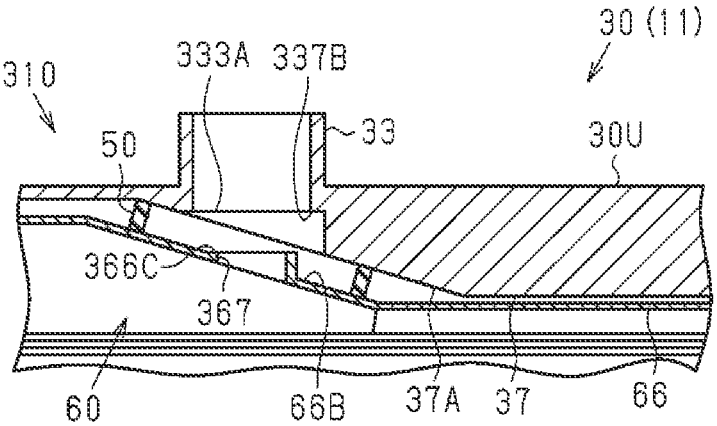
FIG. 8 is a fragmentary sectional view of the CPAP device in a modification.

In the embodiment, an opening position of the first case aperture is not necessarily required to be in the first surface of the housing case but may be in a surface that is among the internal surfaces of the housing case 11 and that is surrounded by the first surface. In an example illustrated in FIG. 8, a second discharge opening 333A of a CPAP device 310 that functions as the first case aperture opens in a separate first opening surface 337B facing in a direction different from the direction of the case slant surface 37A that functions as the first surface. The first opening surface 337B is substantially placed at a center of the upper-side internal surface 37 of the housing case body 30. That is, the first opening surface 337B is surrounded by the case slant surface 37A. The first opening surface 337B is perpendicular to the height direction Td and is not slanted with respect to the surface that is perpendicular to the insertion-ejection direction EEd. Further, in the tank 60 in the example illustrated in FIG. 8, a discharge tank aperture 367 that functions as the first tank aperture opens in a separate second opening surface 366C facing in a direction different from the direction of the tank slant surface 66B that functions as the first facing surface. The second opening surface 366C is substantially placed at a center of the external surface 66A of the lid 66 of the tank 60. That is, the second opening surface 366C is surrounded by the tank slant surface 66B.

Additionally, in the modification described above, the first opening surface 337B and the second opening surface 366C may be nonparallel. At least, it is sufficient if the discharge tank aperture 367 opens at a position facing the second discharge opening 333A, in external surfaces of the tank 60. In the modification described above, for instance, the second opening surface 366C may be omitted from the external surface 66A of the lid 66 of the tank 60, and the discharge tank aperture 367 may open at a position facing the second discharge opening 333A, in the tank slant surface 66B.

In the embodiment, the angle of the slant of the tank slant surface 66B to the surface that is perpendicular to the height direction Td may differ from the angle of the slant of the case slant surface 37A to the surface that is perpendicular to the height direction Td. In such a case, instead of such size adjustment for the first seal member 50 as described above, a portion of the first seal member 50 or the housing case body 30 may undergo elastic deformation, for instance.

In the embodiment, an orientation of the second surface where the second case aperture opens is not limited to the example of the embodiment. For instance, the intersection with both of the insertion-ejection direction EEd and the case slant surface 37A may be made and the orientation may be toward the side of the insertion-ejection opening 34. In this case, the insertion with a push of the tank 60 in the insertion-ejection direction EEd facilitates sealing of a space between the introduction tank aperture 65 and the first discharge opening 25A. Further, as with the case slant surface 37A that functions as the first surface, the end surface 25B of the first discharge portion 25 that functions as the second surface functions as a guide surface when the tank 60 is inserted with a push in the insertion-ejection direction EEd. Furthermore, a difference in orientation between the first surface and the second surface facilitates positioning of the tank 60 in a desired position.

Further, in the embodiment, an orientation of the end surface 25B of the first discharge portion 25 may be an orientation not intersecting with the insertion-ejection direction EEd, for instance. In this case as well, an effect of ensuring the sealability by the case slant surface 37A that functions as the first surface can be obtained.

Further, in the embodiment, the end surface 25B of the first discharge portion 25 may be a surface that is identical to the case slant surface 37A, for instance. In this case as well, when the tank 60 is housed in the housing space of the housing case 11, the sealability between the discharge tank aperture 67 and the second discharge opening 33A can be ensured and the sealability between the introduction tank aperture 65 and the first discharge opening 25A can be ensured.

In the embodiment, configurations of the stopper portions are not limited to the example of the embodiment. For instance, only either one of the turning stopper 80 and the convex portion 36 may be provided as the stopper portion or the configurations of the stopper portions may be omitted. Additionally, positions of the stopper portions are not limited to the example of the embodiment.

In the embodiment, a shape of the tank 60 is not limited to the example of the embodiment. For instance, the shape may be cylindrical or polygonal, as a whole. Instead of the lid 66 of the tank 60, a top wall that cannot be removed from the side walls 63 may be provided. In this case, it is sufficient if water is fed through the second discharge opening 33A, for instance.

In the embodiment, material of the tank 60 is not limited to the example of the embodiment. For instance, the entirety thereof may be metal or the entirety including the contact portion 61A may be resin.

In the embodiment, the second discharge portion 33 of the housing case body 30 extends in parallel with the height direction Td, whereas an extending direction of the second discharge portion 33 may be slanted relative to the height direction Td. Specifically, the thicknesses of the housing case body 30 may be substantially identical and the second discharge portion 33 may extend in a direction in which the second discharge opening 33A opens, that is, the direction that is perpendicular to the case slant surface 37A.

10 CPAP device
11 housing case
20 blowing unit
30 housing case body
33 second discharge portion
33A second discharge opening
34 insertion-ejection opening
37A case slant surface
40 heater
50 first seal member
60 tank
66B tank slant surface 67 discharge tank aperture

The invention claimed is:

1. A CPAP device comprising:

a blowing unit including a built-in blower;

a housing case including the blowing unit;

a water storage tank to be housed in a housing space of the housing case; and a heater to vaporize water stored in the tank, wherein the housing case includes an insertion-ejection opening for insertion and ejection of the tank, a portion of an internal surface of the housing case is a first surface slanted relative to a surface perpendicular to an insertion-ejection direction for the tank through the insertion-ejection opening and facing toward a side of the insertion-ejection opening, a first portion of an external surface of the tank is a first facing surface to come into direct or indirect contact with the first surface when the tank is housed in the housing space and a second portion of the external surface of the tank is a second facing surface opposite the first surface of the tank, the first surface or a surface among internal surfaces of the housing case surrounded by the first surface includes a first case aperture to provide communication between inside and outside of the housing case, the tank includes a first tank aperture to provide communication between inside and outside of the tank, in a position facing the first case aperture when the tank is housed in the housing space, wherein the tank is housed in the housing space such that the first facing surface and the second facing surface are at least partially enclosed by the housing case, wherein a first seal member being an elastic body to seal a space between the first case aperture and the first tank aperture is interposed between the first surface and the first facing surface, and wherein the first surface and the first facing surface are in contact with each other with the first seal member interposed therebetween when the tank is housed in the housing space, wherein at least a portion of the first seal member extends in a shape of bellows.

2. The CPAP device according to claim 1, wherein the heater is mounted in the housing case and is placed on a side opposed to the first surface with the housing space in between.

3. The CPAP device according to claim 2, wherein a second portion of the internal surface of the housing case is a second surface intersecting with both of the insertion-ejection direction and a plane defined by the first surface and facing toward the side of the insertion-ejection opening, the second facing surface comes into contact with the second surface when the tank is housed in the housing space of the housing case, the second surface includes a second case aperture to provide communication between the inside and the outside of the housing case, and the second facing surface includes a second tank aperture to provide communication between the inside and the outside of the tank, in a position facing the second case aperture when the tank is housed in the housing space.

4. The CPAP device according to claim 2, wherein a stopper portion to prevent the tank from being removed through the insertion-ejection opening of the housing case to the outside of the housing case is mounted in the housing case, and the stopper portion is in contact with a contact portion of the tank from the side of the insertion-ejection opening in the insertion-ejection direction when the tank is housed in the housing space of the housing case.

5. The CPAP device according to claim 1, wherein a stopper portion to prevent the tank from being removed through the insertion-ejection opening of the housing case to the outside of the housing case is mounted in the housing case, and the stopper portion is in contact with a contact portion of the tank from the side of the insertion-ejection opening in the insertion-ejection direction when the tank is housed in the housing space of the housing case.

6. The CPAP device according to claim 1, wherein a second portion of the internal surface of the housing case is a second surface intersecting with both of the insertion-ejection direction and the first surface and facing toward the side of the insertion-ejection opening, the second facing surface comes into contact with the second surface when the tank is housed in the housing space of the housing case, the second surface includes a second case aperture to provide communication between the inside and the outside of the housing case, and the second facing surface includes a second tank aperture to provide communication between the inside and the outside of the tank, in a position facing the second case aperture when the tank is housed in the housing space.

7. A CPAP device comprising:

a blowing unit including a built-in blower;

a housing case including the blowing unit;

a water storage tank to be housed in a housing space of the housing case; and a heater to vaporize water stored in the tank, wherein the housing case includes an insertion-ejection opening for insertion and ejection of the tank, a portion of an internal surface of the housing case is a first surface slanted relative to a surface perpendicular to an insertion-ejection direction for the tank through the insertion-ejection opening and facing toward a side of the insertion-ejection opening, a first portion of an external surface of the tank is a first facing surface to come into direct or indirect contact with the first surface when the tank is housed in the housing space and a second portion of the external surface of the tank is a second facing surface opposite the first surface of the tank, the first surface or a surface among internal surfaces of the housing case surrounded by the first surface includes a first case aperture to provide communication between inside and outside of the housing case, the tank includes a first tank aperture to provide communication between inside and outside of the tank, in a position facing the first case aperture when the tank is housed in the housing space, wherein the tank is housed in the housing space such that the first facing surface and the second facing surface are at least partially enclosed by the housing case, wherein a first seal member being an elastic body to seal a space between the first case aperture and the first tank aperture is interposed between the first surface and the first facing surface, and wherein the first surface and the first facing surface are in contact with each other with the first seal member interposed therebetween when the tank is housed in the housing space,

wherein the first seal member is shaped like a circular loop and has a laminated structure comprised of a plurality of layers with respect to a center axis direction of the circular loop of the first seal member, and one of the plurality of layers is comprised of a material differing in elastic modulus from a material of at least another one of the plurality of layers.

8. The CPAP device according to claim 7, wherein a second portion of the internal surface of the housing case is a second surface intersecting with both of the insertion-ejection direction and the first surface and facing toward the side of the insertion-ejection opening, the second facing surface comes into contact with the second surface when the tank is housed in the housing space of the housing case, the second surface includes a second case aperture to provide communication between the inside and the outside of the housing case, and the second facing surface includes a second tank aperture to provide communication between the inside and the outside of the tank, in a position facing the second case aperture when the tank is housed in the housing space.

9. The CPAP device according to claim 7, wherein a stopper portion to prevent the tank from being removed through the insertion-ejection opening of the housing case to the outside of the housing case is mounted in the housing case, and the stopper portion is in contact with a contact portion of the tank from the side of the insertion-ejection opening in the insertion-ejection direction when the tank is housed in the housing space of the housing case.

10. A CPAP device comprising:

a blowing unit including a built-in blower;

a housing case including the blowing unit;

a water storage tank to be housed in a housing space of the housing case; and a heater to vaporize water stored in the tank, wherein the housing case includes an insertion-ejection opening for insertion and ejection of the tank, a portion of an internal surface of the housing case is a first surface slanted relative to a surface perpendicular to an insertion-ejection direction for the tank through the insertion-ejection opening and facing toward a side of the insertion-ejection opening, a first portion of an external surface of the tank is a first facing surface to come into direct or indirect contact with the first surface when the tank is housed in the housing space and a second portion of the external surface of the tank is a second facing surface opposite the first surface of the tank, the first surface or a surface among internal surfaces of the housing case surrounded by the first surface includes a first case aperture to provide communication between inside and outside of the housing case, the tank includes a first tank aperture to provide communication between inside and outside of the tank, in a position facing the first case aperture when the tank is housed in the housing space, wherein the tank is housed in the housing space such that the first facing surface and the second facing surface are at least partially enclosed by the housing case, a second portion of the internal surface of the housing case is a second surface intersecting with both of the insertion-ejection direction and the first surface and facing toward the side of the insertion-ejection opening, the second surface includes a second case aperture to provide communication between the inside and the outside of the housing case, and the second facing surface includes a second tank aperture to provide communication between the inside and the outside of the tank, in a position facing the second case aperture when the tank is housed in the housing space.

11. The CPAP device according to claim 10, wherein the second surface is a surface perpendicular to the insertion-ejection direction for the tank.

12. The CPAP device according to claim 11, wherein a stopper portion to prevent the tank from being removed through the insertion-ejection opening of the housing case to the outside of the housing case is mounted in the housing case, and the stopper portion is in contact with a contact portion of the tank from the side of the insertion-ejection opening in the insertion-ejection direction when the tank is housed in the housing space of the housing case.

13. The CPAP device according to claim 10, wherein a stopper portion to prevent the tank from being removed through the insertion-ejection opening of the housing case to the outside of the housing case is mounted in the housing case, and the stopper portion is in contact with a contact portion of the tank from the side of the insertion-ejection opening in the insertion-ejection direction when the tank is housed in the housing space of the housing case.

14. A CPAP device comprising:

a blowing unit including a built-in blower;

a housing case including the blowing unit;

a water storage tank to be housed in a housing space of the housing case; and a heater to vaporize water stored in the tank, wherein the housing case includes an insertion-ejection opening for insertion and ejection of the tank, a portion of an internal surface of the housing case is a first surface slanted relative to a surface perpendicular to an insertion-ejection direction for the tank through the insertion-ejection opening and facing toward a side of the insertion-ejection opening, a portion of an external surface of the tank is a first facing surface to come into direct or indirect contact with the first surface when the tank is housed in the housing space, the first surface or a surface among internal surfaces of the housing case surrounded by the first surface includes a first case aperture to provide communication between inside and outside of the housing case, the tank includes a first tank aperture to provide communication between inside and outside of the tank, in a position facing the first case aperture when the tank is housed in the housing space, a first seal member being an elastic body to seal a space between the first case aperture and the first tank aperture is interposed between the first surface and the first facing surface, the first surface and the first facing surface are in contact with each other with the first seal member interposed therebetween when the tank is housed in the housing space, a stopper portion to prevent the tank from being removed
    through the insertion-ejection opening of the housing
    case to the outside of the housing case is mounted in the
    housing case, and
the stopper portion is in contact with a contact portion of
    the tank from the side of the insertion-ejection opening
    in the insertion-ejection direction when the tank is
    housed in the housing space of the housing case.

* * * * *